(12) United States Patent
Lynch et al.

(10) Patent No.: US 7,960,588 B2
(45) Date of Patent: Jun. 14, 2011

(54) BENZYL CYCLOALKYL SPHINGOSINE 1-PHOSPHATE RECEPTOR MODULATORS

(75) Inventors: Kevin R. Lynch, Charlottesville, VA (US); Timothy L. Macdonald, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 12/748,981

(22) Filed: Mar. 29, 2010

(65) Prior Publication Data

US 2010/0249074 A1    Sep. 30, 2010

Related U.S. Application Data

(63) Continuation of application No. PCT/US2008/078139, filed on Sep. 29, 2008.

(60) Provisional application No. 60/976,129, filed on Sep. 28, 2007.

(51) Int. Cl.
| | |
|---|---|
| *C07C 215/00* | (2006.01) |
| *C07C 229/00* | (2006.01) |
| *C07F 9/00* | (2006.01) |
| *C07D 333/00* | (2006.01) |
| *C07D 307/00* | (2006.01) |
| *C07D 417/00* | (2006.01) |
| *C07D 261/00* | (2006.01) |
| *C07D 231/00* | (2006.01) |
| *C07D 295/00* | (2006.01) |
| *C07D 207/00* | (2006.01) |
| *A61K 31/66* | (2006.01) |
| *A61K 31/425* | (2006.01) |
| *A61K 31/42* | (2006.01) |
| *A61K 31/415* | (2006.01) |
| *A61K 31/40* | (2006.01) |
| *A61K 31/38* | (2006.01) |
| *A61K 31/34* | (2006.01) |

(52) U.S. Cl. .......... 564/443; 562/441; 558/166; 549/68; 549/480; 548/214; 548/245; 548/246; 548/372.5; 548/557; 548/558; 514/114; 514/372; 514/380; 514/403; 514/404; 514/426; 514/447; 514/472; 514/561; 514/646

(58) Field of Classification Search ....................... None
See application file for complete search history.

(56) References Cited

OTHER PUBLICATIONS

Database CAPLUS on STN, Acc. No. 1982:68469, Vejdelek et al., Collection of Czechoslovak Chemical Communications (1981), 46(9), p. 2234-2244 (abstract).*

* cited by examiner

*Primary Examiner* — Brian J Davis
(74) *Attorney, Agent, or Firm* — Rodney L. Sparks

(57) ABSTRACT

Sphingosine-1-phosphate analogs that are potent, and selective agonists at one or more S1P receptors, specifically the $S1P_1$ receptor type are provided. The disclosed compounds include an optional phosphate moiety as well as compounds with hydrolysis-resistant phosphate surrogates such as phosphonates, alpha-substituted phosphonates, and phosphothionates.

25 Claims, 6 Drawing Sheets

SCHEME 1

Schematic of synthetic scheme for VPC122096

BENZYL CYCLOALKYL SPHINGOSINE 1-PHOSPHATE RECEPTOR MODULATORS

CROSS-REFERENCE TO RELATED APPLICATION

This application is a continuation of International Application No. PCT/US2008/078139, filed on Sep. 29, 2008, which claims priority from U.S. Provisional Application Ser. No. 60/976,129, filed Sep. 28, 2007, the disclosure of which is incorporated herein by reference.

US GOVERNMENT RIGHTS

This invention was made with United States Government support under Grant No. RO1 GM067958 awarded by the National Institutes of Health. The United States Government has certain rights in the invention.

FIELD

The present invention relates to novel sphingosine 1-phosphate analogs with activity at one or more sphingosine 1-phosphate receptors.

BACKGROUND

Sphingosine 1-phosphate (S1P) is a lysophospholipid mediator that has been reported to evoke a variety of cellular responses by stimulation of five members of the endothelial cell differentiation gene (EDG) receptor family. The EDG receptors are G-protein coupled receptors (GPCRs) and on stimulation propagate second messenger signals via activation of heterotrimeric G-protein alpha ($G_\alpha$) subunits and beta-gamma ($G_{\beta\gamma}$) dimers.

Sphingosine 1-phosphate (S1P) has been reported to evoke many responses from cells and tissues. Prominent among these responses is a resistance to apoptosis, changes in cell morphology, cell migration, cell division, angiogenesis and modulation of the immune system via alterations of lymphocyte trafficking. Therefore, S1P receptors are targets for therapy of, for example, neoplastic diseases, autoimmune disorders and rejection of tissue allografts. Sphingosine-1-phosphate signals cells in part via a set of G protein-coupled receptors named $S1P_1$, $S1P_2$, $S1P_3$, $S1P_4$, and $S1P_5$. These receptors share 50-55% identical amino acids and cluster with three other receptors ($LPA_1$, $LPA_2$, and $LPA_3$) for the structurally related lysophosphatidic acid (LPA).

A conformational shift is induced in the G-Protein Coupled Receptor (GPCR) when the ligand binds to that receptor, causing GDP to be replaced by GTP on the α-subunit of the associated G-proteins and subsequent release of the G-proteins into the cytoplasm. The α-subunit then dissociates from the βγ-subunit and each subunit can then associate with effector proteins, which activate second messengers leading to a cellular response. Eventually the GTP on the G-proteins is hydrolyzed to GDP and the subunits of the G-proteins re-associate with each other and then with the receptor. Amplification is believed to play a major role in the general GPCR pathway. The binding of one ligand to one receptor can lead to the activation of many G-proteins, each capable of associating with many effector proteins leading to an amplified cellular response.

S1P receptors have been reported to be both tissue and response specific. Tissue specificity of the S1P receptors is desirable because development of an agonist or antagonist selective for one receptor may localize the cellular response to tissues containing that receptor, limiting unwanted side effects. Response specificity of the S1P receptors is also of importance because it can allow for the development of agonists or antagonists that initiate or suppress certain cellular responses without affecting other responses. For example, the response specificity of the S1P receptors could allow for an S1P mimetic that initiates platelet aggregation without affecting cell morphology.

Sphingosine 1-phosphate is formed as a metabolite of sphingosine in its reaction with sphingosine kinase and is stored in abundance in the aggregates of platelets where high levels of sphingosine kinase exist and S1P lyase is lacking S1P is released during platelet aggregation, accumulates in serum, and has also been found in malignant ascites. Reversible biodegradation of S1P is believed to proceed via hydrolysis by ectophosphatases such as the S1P phosphohydrolase, S1P is degraded irreversibly by S1P lyase.

The physiologic implications of stimulating individual S1P receptors are largely unknown due in part to a lack of receptor type selective ligands. Isolation and characterization of S1P analogs that have potent agonist or antagonist activity for S1P receptors has been limited due to the complication of synthesis derived from the lack of solubility of S1P analogs.

Currently, there is a need for novel, potent, and selective agents that can modulate the S1P receptor; more specifically, $S1P_1$ receptor agonists. There is also a need for pharmacological tools for the further study of the physiological processes associated with agonism of the S1P receptors.

SUMMARY

The present invention provides sphingosine 1-phosphate analogs that are potent, and selective agonists at one or more S1P receptors, specifically the $S1P_1$ receptor type. The disclosed compounds include compounds that have a phosphate moiety as well as compounds with hydrolysis-resistant phosphate surrogates such as phosphonates, alpha-substituted phosphonates (particularly where the alpha-substitution is a halogen), and phosphothionates. In addition, the invention provides pro-drugs, such as primary alcohol containing compounds that are activated or converted, (e.g., phosphorylated) in vitro, e.g., by sphingosine kinase enzyme, most particularly sphingosine kinase type 2 (SPHK2).

Accordingly, the invention provides sphingosine 1-phosphate analogs having formula (I) or formula (II):

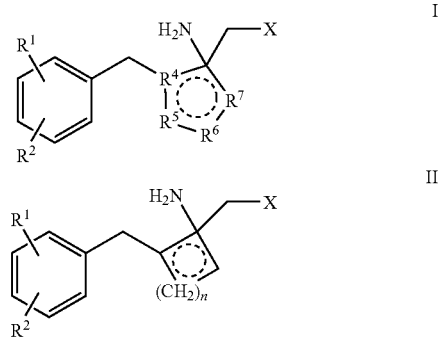

wherein $R^4$ is C, CH, or N; $R^5$, $R^6$ and $R^7$ are independently is CH, $CH_2$, O, S, N, or $NR^3$; wherein $R^3$ is hydrogen, or an ($C_1$-$C_{10}$) alkyl group;

X is hydroxyl (—OH), carboxylic acid (—COOH), methylene carboxylic acid (—$CH_2COOH$), alpha-substituted methylene carboxylic acid, phosphate (—OPO$_3$H$_2$), phosphonate (—CH$_2$PO$_3$H$_2$), or alpha-substituted phosphonate;

R$^1$ is hydrogen, halo, tri-fluoromethyl, (C$_1$-C$_{10}$-alkyl, (C$_1$-C$_{10}$) alkyl substituted with halo, hydroxy, alkoxy, or cyano;

R$^2$ is hydrogen, halo, (C$_1$-C$_{20}$)alkyl, (C$_1$-C$_{20}$)alkoxy; (C$_2$-C$_{26}$)alkoxyalkyl; (C$_2$-C$_{20}$)alkenyl, (C$_2$-C$_{20}$)alkynyl, (C$_3$-C$_{12}$)cycloalkyl, (C$_1$-C$_{20}$)alkyl-(C$_3$-C$_{12}$)cycloalkyl, (C$_6$-C$_{10}$)aryl, (C$_1$-C$_{20}$)alkyl(C$_6$-C$_{10}$)aryl, (C$_6$-C$_{10}$)aryl (C$_1$-C$_{20}$)alkyl, and aryl substituted arylalkyl; wherein one or more of the carbon atoms in the R$^2$ groups can be independently replaced with non-peroxide oxygen, sulfur or NR$^8$; wherein R$^8$ is hydrogen, or an (C$_1$-C$_{10}$) alkyl group;

the alkenyl, alkynyl, cycloalkyl, aryl, heterocyclic, or heteroaryl groups of R$^1$, R$^2$, or X are optionally substituted with 1, 2, 3, or 4 groups where the substituent groups are independently hydroxy, halo, cyano, (C$_1$-C$_{10}$)alkyl, (C$_1$-C$_{10}$)alkoxy, C$_6$-aryl, (C$_7$-C$_{24}$)arylalkyl, oxo (=O), or imino (=NR$^a$); R$^a$ is hydrogen, or (C$_1$-C$_{10}$)alkyl; n is 0, 1, 2, 3, or 4;

indicates one or more optional double bonds, and the alkyl groups of R$^3$ are optionally substituted with 1, or 2 hydroxy groups;

or a pharmaceutically acceptable salt or ester thereof.

In another aspect, the invention also provides esters of any of the compounds of formula (I) or formula (II), e.g., phosphate esters having formula (III) or formula (IV).

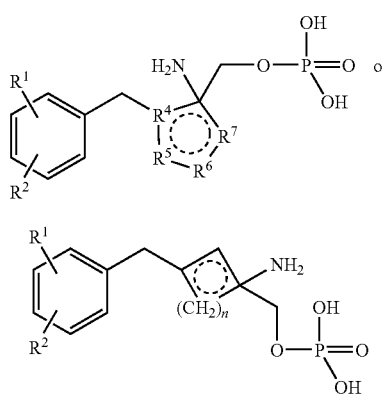

wherein R$^1$, R$^2$, R$^4$, R$^5$, R$^6$, R$^7$ and n are as described above, wherein the ester function can be added to form pro-drugs to increase oral availability. In another aspect, the invention provides enantiomers and stereoisomers of the compounds having formulas I, II, III or IV.

In another aspect, the invention provides pro-drugs of the compounds of formula (I) or (II). In another aspect, the invention also provides compounds of formula (I), formula (II), pharmaceutically acceptable salts, esters thereof (e.g., formula (III), or formula (IV)), or any combination thereof for use in medical therapy.

In another aspect, the present invention also provides:
compounds that can be agonists at the S1P type 1 receptor, and thus evoke lymphopenia, for up to about five days, or longer, when introduced into animals;
compounds of the invention that can be selective agonists for the S1P$_1$, S1P$_4$, and S1P$_5$ receptors, and can have a long duration of action, e.g., longer than FTY-720 (fingolimod);
pharmaceutical compositions comprising a compound of formula (I), formula (II), pharmaceutically acceptable salts, esters thereof (e.g., formula (III), or formula (IV)), or any combination thereof and a pharmaceutically acceptable carrier or excipient;
a method for prevention or treatment of autoimmune diseases, such as, uveitis, type I diabetes, rheumatoid arthritis, inflammatory bowel diseases, and, more particularly, multiple sclerosis;
a method for prevention or treatment of chronic pain, specifically neuropathic pain including but not limited to pain associated with postherpetic neuralgia and diabetes;
a method for prevention or treatment of progressive dementia or brain degenerative diseases;
a method for altering lymphocyte trafficking to prolong allograft survival, e.g., solid organ transplants, treatment of graft vs. host disease, bone marrow transplantation, etc.;
a method for treating or preventing cancer progression via inhibition of autotaxin, e.g., by preventing or inhibiting angiogenesis in a tumor;
a method for prevention or treatment of a pathological condition or symptom in a mammal, wherein the activity of sphingosine 1-phosphate receptors is implicated;
a method for prevention or treatment of a pathological condition or symptom in a mammal, wherein the activity S1P lyase implicated and inhibition of the S1P lyase is desired;
wherein the methods comprise administering to a mammal (e.g., a human) in need of such treatment, an effective amount of a compound of formula (I), formula (II) or a pharmaceutically acceptable salt or ester thereof; or
the use of a compound of formula (I), formula (II), or a pharmaceutically acceptable salt thereof to prepare a medicament for preventing or inhibiting autoimmune diseases, prevention or treatment of chronic pain, prevention or treatment of progressive dementia or brain degenerative diseases, altering lymphocyte trafficking or treating or preventing angiogenesis in a tumor in a mammal (e.g., a human).

The invention also provides novel intermediates and processes disclosed herein that are useful for preparing compounds of formula (I), formula (II), formula (III) or formula (IV), including the generic and specific intermediates as well as the synthetic processes described in the Charts and Examples herein.

DETAILED DESCRIPTION

Figure 1:
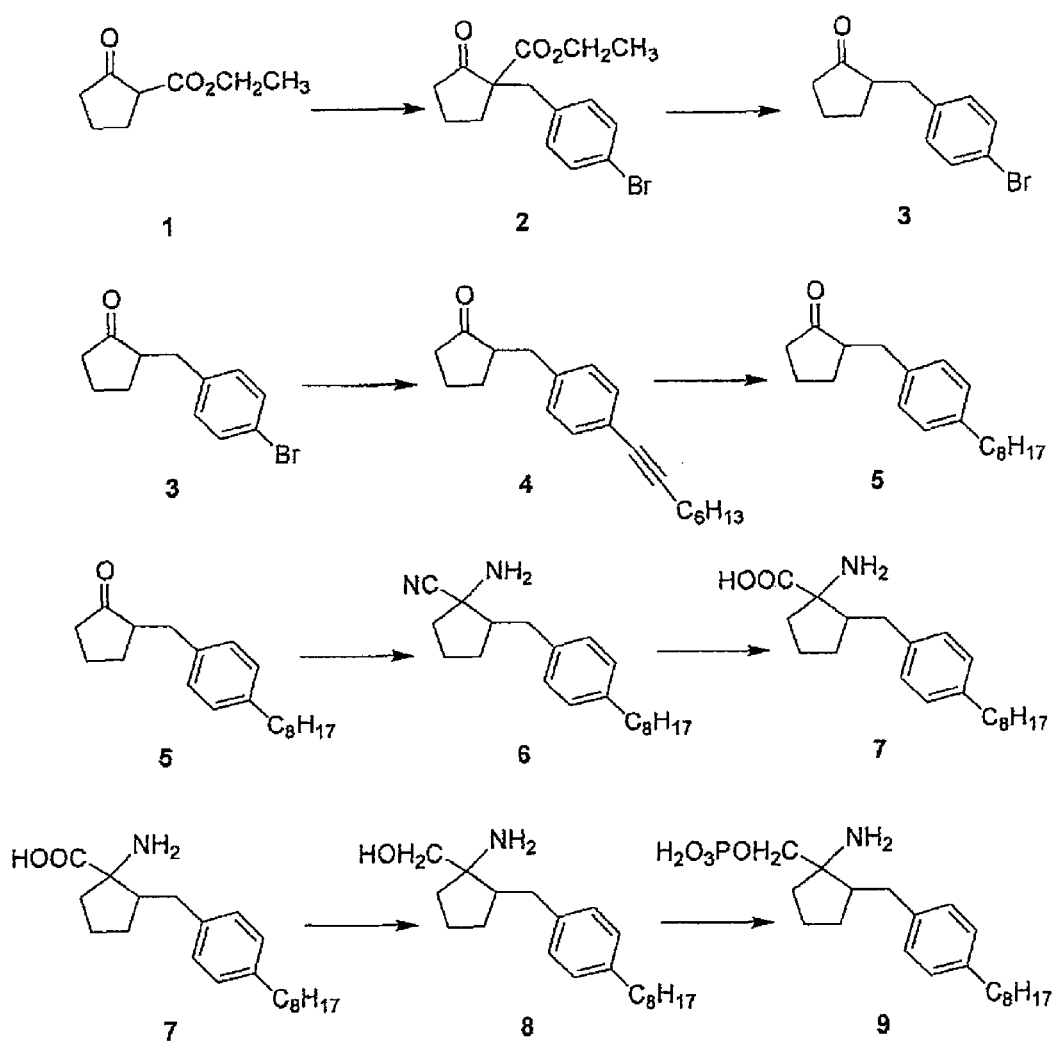
FIG. 1 illustrates a synthetic scheme for the preparation of compound VPC122096.

The following abbreviations are used herein: S1P, sphingosine-1-phosphate; $S1P_{1-5}$, S1P receptor types; GPCR, G-protein coupled receptor; SAR, structure-activity relationship; EDG, endothelial cell differentiation gene; EAE, experimental autoimmune encephalomyelitis; NOD non-obese diabetic; TNFα, tumor necrosis factor alpha; HDL, high density lipoprotein; and RT-PCR, reverse transcriptase polymerase chain reaction In describing and claiming the invention, unless otherwise defined, all technical and scientific terms used herein have the same meaning as commonly understood by a person of ordinary skill in the art to which this invention belongs. Although any materials and methods similar or equivalent to those described herein can be used in the practice or testing of the present invention, the preferred materials and methods are described herein. Each of the following terms has meaning associated with it in this section. Specific and preferred values listed below for radicals, substituents, and ranges are for illustrations only; they do not exclude other defined values or other values within defined ranges for the radicals and substituents.

The terms "a," "an," "the," "at least one," and "one or more" are used interchangeably herein to refer to one or to more than one (i.e., to at least one) of the grammatical object of the article. By way of example, "an element" means one element or more than one element.

"Receptor agonists" are defined as compounds that mimic the action of S1P at its receptors but with differing potency or efficacy.

The term "receptor agonists" are compounds that mimic the action of S1P at one or more of its receptors but may have differing potency or efficacy.

The term "receptor antagonists" are compounds that 1) lack intrinsic agonist activity and 2) block agonist (e.g., S1P) activation of the S1P receptor(s), often in a manner that is both fully surmountable and reversible ('competitive antagonist').

The term "affected cell" refers to a cell of a subject afflicted with a disease or disorder, which affected cell has an altered phenotype relative to a subject not afflicted with a disease or disorder. Cells or tissue are "affected" by a disease or disorder if the cells or tissue have an altered phenotype relative to the same cells or tissue in a subject not afflicted with a disease or disorder. A disease or disorder is "alleviated" if the severity of a symptom of the disease or disorder, the frequency with which such a symptom is experienced by a patient, or both, is reduced.

An "analog" of a chemical compound is a compound that, by way of example, resembles another in structure but is not necessarily an isomer (e.g., 5-fluorouracil is an analog of thymine).

The terms "cell," "cell line," and "cell culture" may be used interchangeably.

A "control" cell, tissue, sample, or subject is a cell, tissue, sample, or subject of the same type as a test cell, tissue, sample, or subject. The control may, for example, be examined at precisely or nearly the same time the test cell, tissue, sample, or subject is examined. The control may also, for example, be examined at a time distant from the time at which the test cell, tissue, sample, or subject is examined, and the results of the examination of the control may be recorded so that the recorded results may be compared with results obtained by examination of a test cell, tissue, sample, or subject. The control may also be obtained from another source or similar source other than the test group or a test subject, where the test sample is obtained from a subject suspected of having a disease or disorder for which the test is being performed.

A "test" cell, tissue, sample, or subject is one being examined.

A "pathoindicative" cell, tissue, or sample is one which, when present, is an indication that the animal in which the cell, tissue, or sample is located (or from which the tissue was obtained) is afflicted with a disease or disorder. By way of example, the presence of one or more breast cells in a lung tissue of an animal is an indication that the animal is afflicted with metastatic breast cancer.

A tissue "normally comprises" a cell if one or more of the cell are present in the tissue in an animal not afflicted with a disease or disorder.

The word "detect" and its grammatical variants is meant to refer to measurement of the species without quantification, whereas use of the word "determine" or "measure" with their grammatical variants are meant to refer to measurement of the species with quantification. The terms "detect" and "identify" are used interchangeably herein.

A "detectable marker" or a "reporter molecule" is an atom or a molecule that permits the specific detection of a compound comprising the marker in the presence of similar compounds without a marker. Detectable markers or reporter molecules include, but are not limited to, radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

A "disease" is a state of health of an animal wherein the animal cannot maintain homeostasis, and wherein if the disease is not ameliorated then the animal's health continues to deteriorate.

A "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

An "effective amount" means an amount sufficient to produce a selected effect. A "therapeutically effective amount" of a compound is that amount of compound which is sufficient to provide a beneficial effect to the subject to which the compound is administered. For example, an effective amount of an S1P receptor agonist is an amount that decreases the cell signaling activity of the S1P receptor.

A "therapeutic" treatment is a treatment administered to a subject who exhibits signs of pathology for the purpose of diminishing or eliminating those signs.

The term "treating" includes prophylaxis of the specific disorder or condition, or alleviation of the symptoms associated with a specific disorder or condition or preventing or eliminating said symptoms. A "prophylactic" treatment is a treatment administered to a subject who does not exhibit signs of a disease or exhibits only early signs of the disease for the purpose of decreasing the risk of developing pathology associated with the disease.

A "functional" molecule is a molecule in a form in which it exhibits a property by which it is characterized. By way of example, a functional enzyme is one which exhibits the characteristic catalytic activity by which the enzyme is characterized.

The term "inhibit" refers to the ability of a disclosed compound to reduce or impede a described function. Preferably, inhibition is by at least 10%, more preferably by at least 25%, even more preferably by at least 50%, and most preferably, the function is inhibited by at least 75%.

A "sample" refers preferably to a biological sample from a subject, including, but not limited to, normal tissue samples, diseased tissue samples, biopsies, blood, saliva, feces, semen, tears, and urine. A sample can also be any other source of material obtained from a subject, which contains cells, tissues, or fluid of interest. A sample can also be obtained from cell or tissue culture.

The term "standard," as used herein, refers to something used for comparison. For example, it can be a known standard agent or compound which is administered or added to a control sample and used for comparing results when measuring said compound in a test sample. Standard can also refer to an "internal standard", such as an agent or compound which is added at known amounts to a sample and is useful in determining such things as purification or recovery rates when a sample is processed or subjected to purification or extraction procedures before a marker of interest is measured.

A "subject" of analysis, diagnosis, or treatment is an animal. Such animals include mammals, preferably a human.

The term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure.

The term "parenteral" means not through the alimentary canal but by some other route such as subcutaneous, intramuscular, intraspinal, or intravenous.

A "derivative" of a compound refers to a chemical compound that may be produced from another compound of similar structure in one or more steps, as in replacement of hydrogen by an alkyl, acyl, or amino group.

The term "pharmaceutically acceptable carrier" includes any of the standard pharmaceutical carriers known in the art, such as a phosphate buffered saline solution, hydroxypropyl beta-cyclodextrins (HO-propyl beta cyclodextrins), water, emulsions such as an oil/water or water/oil emulsion, and various types of wetting agents. The term also encompasses any of the agents approved by a regulatory agency of the US Federal government or listed in the US Pharmacopeia for use in animals, including humans.

The term "pharmaceutically-acceptable salt" refers to salts which retain the biological effectiveness and properties of the compounds of the present invention and which are not biologically or otherwise undesirable. In many cases, the compounds of the present invention are capable of forming acid or base salts by virtue of the presence of amino or carboxyl groups or groups similar thereto.

"Instructional material" includes a publication, a recording, a diagram, or any other medium of expression which can be used to communicate the usefulness of the composition of the invention for its designated use. The instructional material of the kit of the invention may, for example, be affixed to a container that contains the composition or be shipped together with a container that contains the composition. Alternatively, the instructional material may be shipped separately from the container with the intention that the instructional material and the composition be used cooperatively by the recipient.

The disclosed method includes a kit comprising an inhibitor identified herein and instructional material which describes administration of the inhibitor or a composition comprising the inhibitor to a cell or an animal. This should be construed to include other embodiments of kits that are known to those skilled in the art, such as a kit comprising a (preferably sterile) solvent for dissolving or suspending the disclosed composition prior to administering the compound to a cell or an animal. Preferably the animal is a human.

It will be appreciated by those skilled in the art that the disclosed compounds having a chiral center may exist in and be isolated in optically active and racemic forms. Some compounds may exhibit polymorphism. It is to be understood that the disclosed compounds encompass any racemic, optically-active, polymorphic, or stereoisomeric form, or mixtures thereof, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine S1P agonist activity using the standard tests described herein, or using other similar tests which are well known in the art.

In cases where compounds are sufficiently basic or acidic to form acid or base salts, use of the compounds as salts may be appropriate. Examples of acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Inorganic salts may also be formed, including hydrochloride, sulfate, nitrate, bicarbonate, and carbonate salts.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

Pharmaceutically-acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and triamines where at least two of the substituents on the amine are different and are alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group. Examples of amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like. It should also be understood that other carboxylic acid derivatives would be useful in the practice of this invention, for example, carboxylic acid amides, including carboxamides, lower alkyl carboxamides, dialkyl carboxamides, and the like.

Acceptable salts may be obtained using standard procedures well known in the art, for example by reacting a sufficiently basic compound such as an amine with an acid affording a physiologically acceptable anion. Alkali metal (for example, sodium, potassium or lithium) or alkaline earth metal (for example calcium) salts of organic (e.g., carboxylic) acids can also be made.

Processes for preparing compounds of formula (I), formula (II) or for preparing intermediates useful for preparing compounds of formula (I) or formula (II) are provided as further embodiments of the invention. Intermediates useful for preparing compounds of formula (I) or formula (II) are also provided as further embodiments of the invention.

The term "halogen" or "halo" includes bromo, chloro, fluoro, and iodo.

The term "haloalkyl" as used herein refers to an alkyl radical bearing at least one halogen substituent, for example, chloromethyl, fluoroethyl or trifluoromethyl and the like.

The term "alkyl or $C_1$-$C_{20}$ alkyl," as used herein, represents a branched or linear alkyl group having from one to twenty carbon atoms. Typically $C_1$-$C_{20}$ alkyl groups include, but are not limited to, methyl, ethyl, n-propyl, iso-propyl, butyl, iso-butyl, sec-butyl, tert-butyl, pentyl, hexyl, heptyl, octyl, and the like. The term "alkenyl or $C_2$-$C_{20}$ alkenyl," as used herein, represents an olefinically unsaturated branched or linear group having from 2 to 20 carbon atoms and at least one double bond. Examples of such groups include, but are not limited to, 1-propenyl, 2-propenyl, 1,3-butadienyl, 1-butenyl, hexenyl, pentenyl, and the like. The term "alkynyl or $C_2$-$C_{20}$ alkynyl," refers to an unsaturated branched or linear group having from 2 to 20 carbon atoms and at least one triple bond. Examples of such groups include, but are not limited to, 1-propynyl, 2-propynyl, 1-butynyl, 2-butynyl, 1-pentynyl, and the like. The term "$C_3$-$C_{12}$cycloalkyl," represents cyclopropyl, cyclobutyl, cyclopentyl, cyclohexyl, cycloheptyl, cyclooctyl and the like.

As used herein, the term "optionally substituted" refers to zero, one, two, three, or four substituents, wherein the substituents are each independently selected. Each of the independently selected substituents may be the same or different than other substituents. The substituent groups are independently hydroxy, halo, cyano, ($C_1$-$C_{10}$)alkyl, ($C_1$-$C_{10}$)alkoxy, $C_6$-aryl, ($C_7$-$C_{24}$)arylalkyl, oxo (=O), or imino (=$NR^a$), where $R^a$ is hydrogen, or ($C_1$-$C_{10}$)alkyl.

As used herein the term "aryl" refers to a mono or bicyclic $C_6$-$C_{10}$ carbocyclic ring system having one or two aromatic rings including, but not limited to, phenyl, benzyl, naphthyl, tetrahydronaphthyl, indanyl, indenyl, and the like.

As used herein "optionally substituted aryl" includes aryl compounds having from zero to four substituents, and a substituted aryl includes aryl compounds having one to three substituents, wherein the substituents include groups such as, for example, alkyl, halo or amino substituents.

The term "arylalkyl" refers to any aryl group which is attached to the parent moiety via the alkyl group, e.g., aryl ($C_1$-$C_{20}$alkyl). Thus, the term ($C_5$-$C_6$ aryl)($C_5$-$C_8$ alkyl) refers to a five or six membered aromatic ring that is attached to the parent moiety via the $C_5$-$C_8$ alkyl group.

The term "heterocyclic group" refers to an optionally substituted mono- or bicyclic carbocyclic ring system containing from one to three heteroatoms wherein the heteroatoms are oxygen, sulfur, or nitrogen.

As used herein the term "heteroaryl" refers to an optionally substituted mono- or bicyclic carbocyclic ring system having one or two aromatic rings containing from one to three heteroatoms and includes, but is not limited to, furyl, thienyl, pyridyl and the like.

The term "bicyclic" represents either an unsaturated or saturated stable 7- to 12-membered bridged or fused bicyclic carbon ring. The bicyclic ring may be attached at any carbon atom which affords a stable structure. The term includes, but is not limited to, naphthyl, dicyclohexyl, dicyclohexenyl, and the like.

The compounds of the present invention can contain one or more asymmetric centers in the molecule. In accordance with the present invention any structure that does not designate the stereochemistry is to be understood as embracing all the various optical isomers, as well as racemic mixtures thereof.

The compounds of the present invention may exist in tautomeric forms and the invention includes both mixtures and separate individual tautomers. For example, the following structure:

is understood to represent a mixture of the structures:

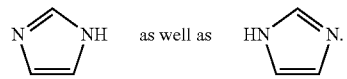

The terms 16:0, 18:0, 18:1, 20:4 or 22:6 hydrocarbon refers to a branched or straight alkyl or alkenyl group, wherein the first integer represents the total number of carbons in the group and the second integer represent the number of cis double bonds in the group.

An "S1P modulating agent" refers a compound or composition that is capable of inducing a detectable change in S1P receptor activity in vivo or in vitro (e.g., at least 10% increase or decrease in S1P activity as measured by a given assay such as the bioassay described in the examples and known in the art. "S1P receptor," as used herein, refers to all of the S1P receptor subtypes (for example, the S1P receptors $S1P_1$, $S1P_2$, $S1P_3$, $S1P_4$, and $S1P_5$), unless the specific subtype is indicated.

The term "EC$_{50}$ of an agent" refers to that concentration of an agent at which a given activity, including binding of sphingosine or other ligand of an S1P receptor or a functional activity of a S1P receptor (e.g., a signaling activity), is 50% maximal for that S1P receptor. Stated differently, the EC$_{50}$ is the concentration of agent that gives 50% activation, when 100% activation is set at the amount of activity of the S1P receptor which does not increase with the addition of more ligand/agonist and 0% is set at the amount of activity in the assay in the absence of added ligand/agonist.

The term "phosphate analog", "phosphonate analog" or "phosphate ester" comprise analogs of phosphate and phosphonate wherein the phosphorous atom is in the +5 oxidation state and one or more of the oxygen atoms is replaced with a non-oxygen moiety, including for example, the phosphate analogs phosphorothioate, phosphorodithioate, phosphoroselenoate, phosphorodiselenoate, phosphoroanilothioate, phosphoranilidate, phosphoramidate, boronophosphates, and the like, including associated counterions, e.g., hydrogen, NH$_4$, Na, and the like if such counterions are present. The term "alpha-substituted phosphonate" includes phosphonate (—CH$_2$PO$_3$H$_2$) groups that are substituted on the alpha-carbon such as —CHFPO$_3$H$_2$, —CF$_2$PO$_3$H$_2$, —CHOHPO$_3$H$_2$, —C(=O)PO$_3$H$_2$) and the like.

The present invention is provides to sphingosine 1-phosphate (S1P) analogs that have activity as receptor agonists at one or more S1P receptors, specifically the S1P$_1$, S1P$_4$ and S1P$_5$ receptor types. The invention includes both compounds that have a phosphate moiety as well as compounds with hydrolysis-resistant phosphate surrogates such as phosphonates, alpha-substituted phosphonates particularly where the alpha substitution is a halogen and phosphothionates.

In one embodiment of the S1P receptor agonists have the general structure of Formula (IIA):

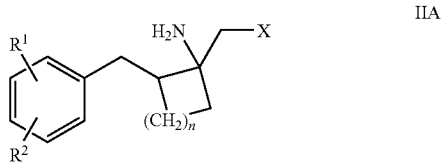

wherein n is 0, 1, 2, 3, or 4; X is hydroxyl (—OH), carboxylic acid (—COOH), methylene carboxylic acid (—CH$_2$COOH), alpha-substituted carboxylic acid, phosphate (—OPO$_3$H$_2$), phosphonate (—CH$_2$PO$_3$H$_2$), or alpha-substituted phosphonate (including: —CHFPO$_3$H$_2$, —CF$_2$PO$_3$H$_2$, —CHOHPO$_3$H$_2$, —C(=O)PO$_3$H$_2$);

wherein R$^1$ is hydrogen, halogens (wherein F or Cl are preferred halogens), (C$_1$-C$_6$) alkyl, such as, methyl, ethyl, and propyl, or halo-, hydroxy-, alkoxy-, cyano-substituted (C$_1$-C$_6$) alkyl, such as, tri-fluoromethyl; R$^2$ is alkyl, alkenyl, alkynyl, alkyl substituted aryl, alkyl substituted cycloalkyl, arylalkyl, or arylalkyl substituted aryl. In R$^2$ the chain lengths of 5-8 carbon atoms are preferred; or a pharmaceutically acceptable salt thereof.

The present invention also provides esters of any of the compounds of formula (II), e.g., phosphate esters, wherein the ester function can be added to form pro-drugs to increase oral availability.

In a preferred embodiment, in compounds having formula (II) R$^1$ is H, halo (F or Cl preferred), methyl, tri-fluoromethyl, ethyl, propyl or other lower alkyl (C$_1$-C$_6$) or halo-, hydroxy-, alkoxy-, cyano-substituted lower alkyl group; and R$_2$ is alkyl, alkenyl, alkynyl, alkyl (optionally substituted aryl), alkyl (optionally substituted cycloalkyl), arylalkyl, and arylalkyl (optionally substituted aryl) with chain lengths of 5-8 carbon atoms preferred.

Potential uses of an S1P receptor agonist pro-drugs (S1P$_1$ receptor type selective agonists preferred) include, but are not limited to altering lymphocyte trafficking as a method of treatment for autoimmune pathologies such as uveitis, type I diabetes, rheumatoid arthritis, inflammatory bowel diseases, and, most particularly, multiple sclerosis. "Treatment" of multiple sclerosis includes the various forms of the disease including relapsing-remitting, chronic progressive, etc., and the S1P receptor agonists can be used alone or in conjunction with other agents to relieve signs and symptoms of the disease as well as prophylactically.

In addition, the compounds of the invention can be used for altering lymphocyte trafficking is a method for prolonging allograft survival, for example solid organ transplants, treatment of graft vs. host disease, bone marrow transplantation, and the like.

The disclosed compounds can be used to inhibit autotaxin. Autotaxin, a plasma phosphodiesterase, has been demonstrated to undergo end product inhibition. Autotaxin hydrolyzes several substrates to yield lysophosphatidic acid and sphingosine 1-phosphate, and has been implicated in cancer progression and angiogenesis. Therefore, S1P receptor agonist pro-drugs such as VPC122096 can be used to inhibit autotaxin. This activity may be combined with agonism at S1P receptors or may be independent of such activity.

In addition, compounds of the invention can be useful for inhibition of S1P lyase. S1P lyase is an intracellular enzyme that irreversibly degrades S1P. Inhibition of S1P lyase disrupts lymphocyte trafficking with concomitant lymphopenia. Accordingly, S1P lyase inhibitors can be useful in modulating immune system function. Therefore, pro-drugs such as VPC122096 can be used to inhibit S1P lyase. This inhibition could be in concert with S1P receptor activity, or be independent of activity at any S1P receptor.

The present invention is also includes pharmaceutical compositions comprising the compounds of the present invention. More particularly, such compounds can be formulated as pharmaceutical compositions using standard pharmaceutically acceptable carriers, fillers, solubilizing agents and stabilizers known to those skilled in the art. For example, a pharmaceutical composition comprising a compound of the invention, or analog, derivative, or modification thereof, as described herein, is used to administer the appropriate compound to a subject.

The compounds of the invention are useful for treating a disease or disorder including administering to a subject in need thereof of a therapeutically acceptable amount of a compound of formula (I), or a pharmaceutical composition comprising a therapeutically effective amount of a compound of formula (I) or formula (II), and a pharmaceutically-acceptable carrier.

The values listed below for radicals, substituents, and ranges, are for illustration only; they do not exclude other defined values or other values within defined ranges for the radicals and substituents.

Exemplary values for lower alkyl group are ethyl or propyl.
Exemplary values for halo are fluorine or chlorine.
Exemplary values for X are hydroxy or OPO$_3$H$_2$.
Alpha-substituted phosphonate includes —CHFPO$_3$H$_2$, —CF$_2$PO$_3$H$_2$, —CHOHPO$_3$H$_2$, —C(=O)PO$_3$H$_2$) or thiophosphate (OPO$_2$SH$_2$).
An exemplary value for R$^1$ is hydrogen.

An exemplary value for $R^2$ is an alkyl group with a chain length of 5-8 carbon atoms.

Additional exemplary values for $R^2$ are heptyl, octyl, nonyl, —O-heptyl, $CH_3$—O—$CH_2$—$CH_2$—$CH_2$—$CH_2$—$CH_2$—$CH_2$—, —C(=O)heptyl, or $CH_3$—$CH_2$—O—$CH_2$—$CH_2$—O—$CH_2$—$CH_2$—O—.

Additional exemplary values for the $R^2$ alkyl groups are octyl, $CH_3$—O—$CH_2$—$CH_2$—$CH_2$—$CH_2$—$CH_2$—$CH_2$—, or —O-heptyl.

Another exemplary $R^2$ alkyl group is octyl.

Exemplary values for n are 2 or 3.

Exemplary cycloalkyl or heterocyclic groups having a double bond include:

Exemplary compounds have the $R^2$ group placed para to the cycloalkyl ring.

Exemplary compounds have the $R^1$ group placed ortho or meta to $R^2$.

Exemplary compounds have the $R^2$ group placed para to the benzylic cycloalkyl group (i.e., 1,4).

Non-limiting examples of esters of the compounds of the invention include compounds where the X group is;

wherein Y is O, $CH_2$, CHOH, CHF, $CF_2$, or and $R^9$ and $R^{10}$ are independently alkoxy, alkenyloxy, alkynyloxy, aryloxy, wherein $R^{11}$ is $C_1$-$C_4$ alkyl, $C_2$-$C_4$ alkenyl, $C_2$-$C_4$ alkynyl, or optionally substituted aryl. Preferred $R^9$ and $R^{10}$ groups are alkoxy, A synthetic route to prepare VPC122096 is provided in the scheme in FIG. 1. Additional compounds of formula (I) or formula (II) can be prepared by a person skilled in the art using known modifications to procedures from the schemes and detailed descriptions in the specific examples below.

An exemplary compound of formula (II) is VPC122096, where X is OH, $R^1$ is hydrogen, $R^2$ is octane ($C_8H_{17}$), n is 2, and the $R^2$ group is in the para position on the phenyl ring. The formula is:

VPC122096

Another exemplary compound of formula (II) is VPC122093, where X is OH, $R^1$ is hydrogen, $R^2$ is octane ($C_8H_{17}$), n is 3, and the $R^2$ group is in the para position on the phenyl ring. The formula is:

VPC122093

Another exemplary compound of formula (II) is VPC122097, where X is OH, $R^1$ is hydrogen, $R^2$ is octane ($C_8H_{17}$), n is 4, and the $R^2$ group is in the para position on the phenyl ring. The formula is:

VPC122097

The invention also includes the following isomers:

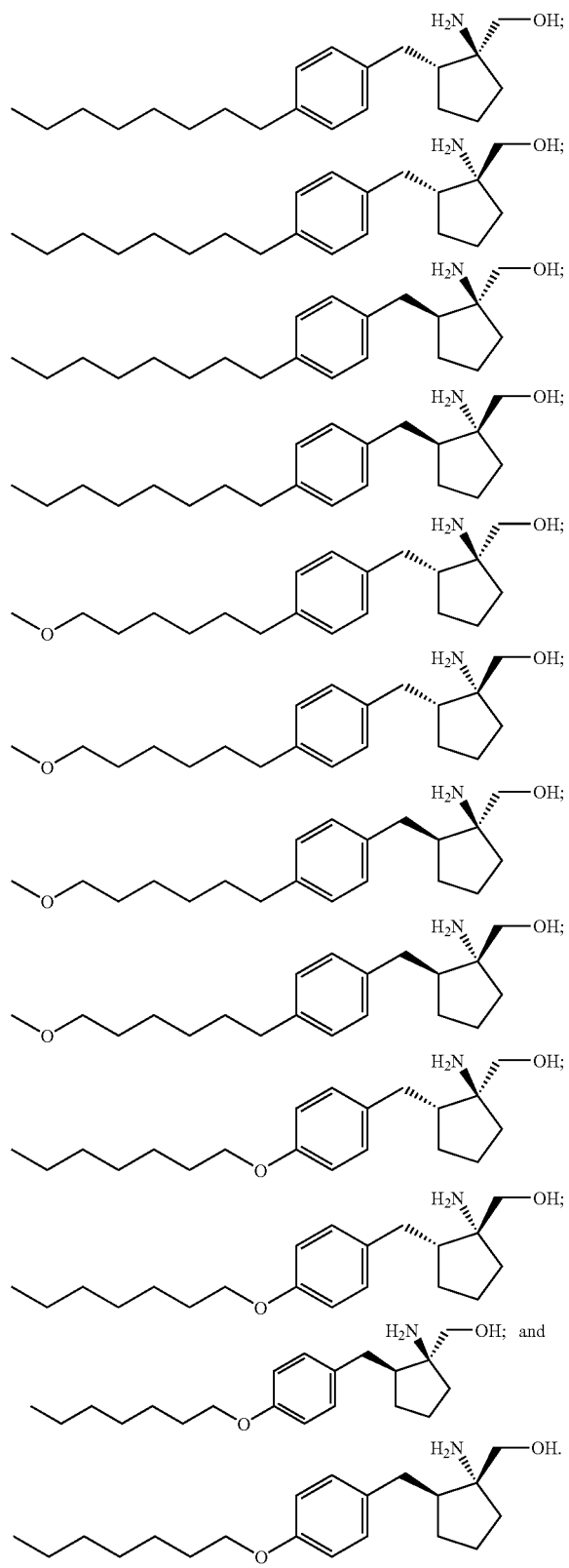

Another exemplary compound of formula (II) is VPC122096-P where X is OPO$_3$H$_2$, R$^1$ is hydrogen, R$^2$ is octane (C$_8$H$_{17}$), n is 2, and the R$^2$ group is in the para position on the phenyl ring. The formula is:

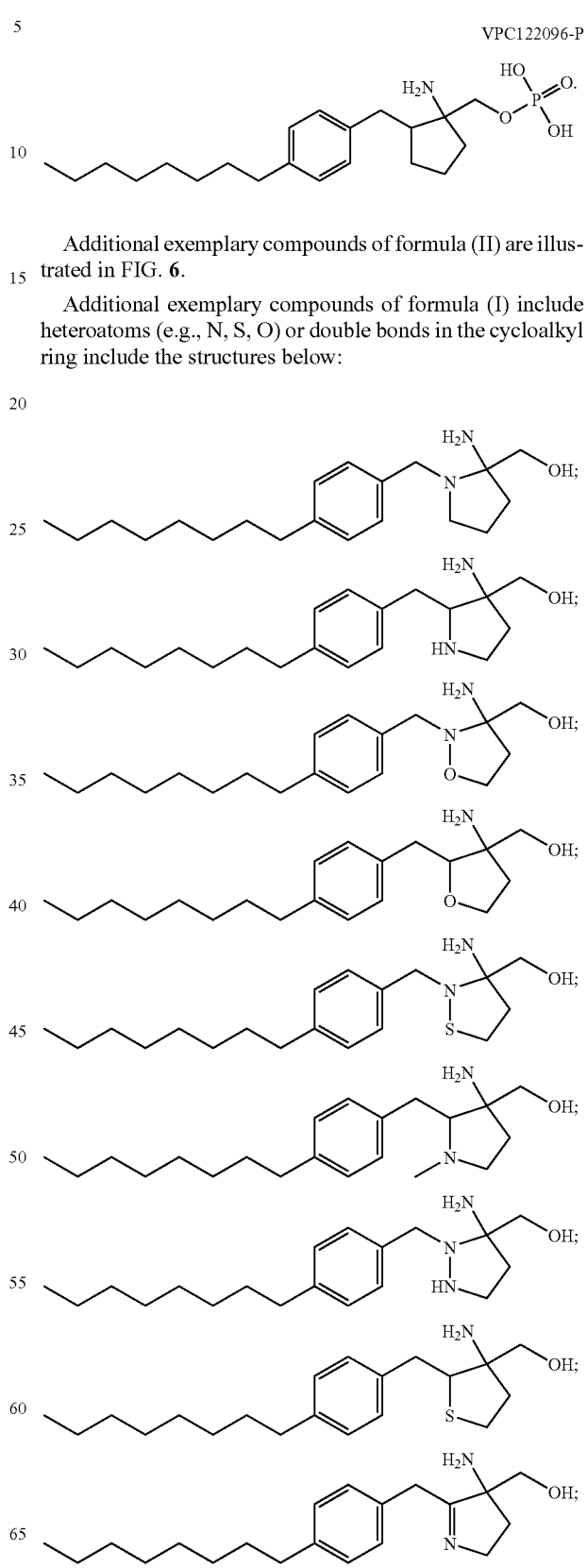

Figure 6:
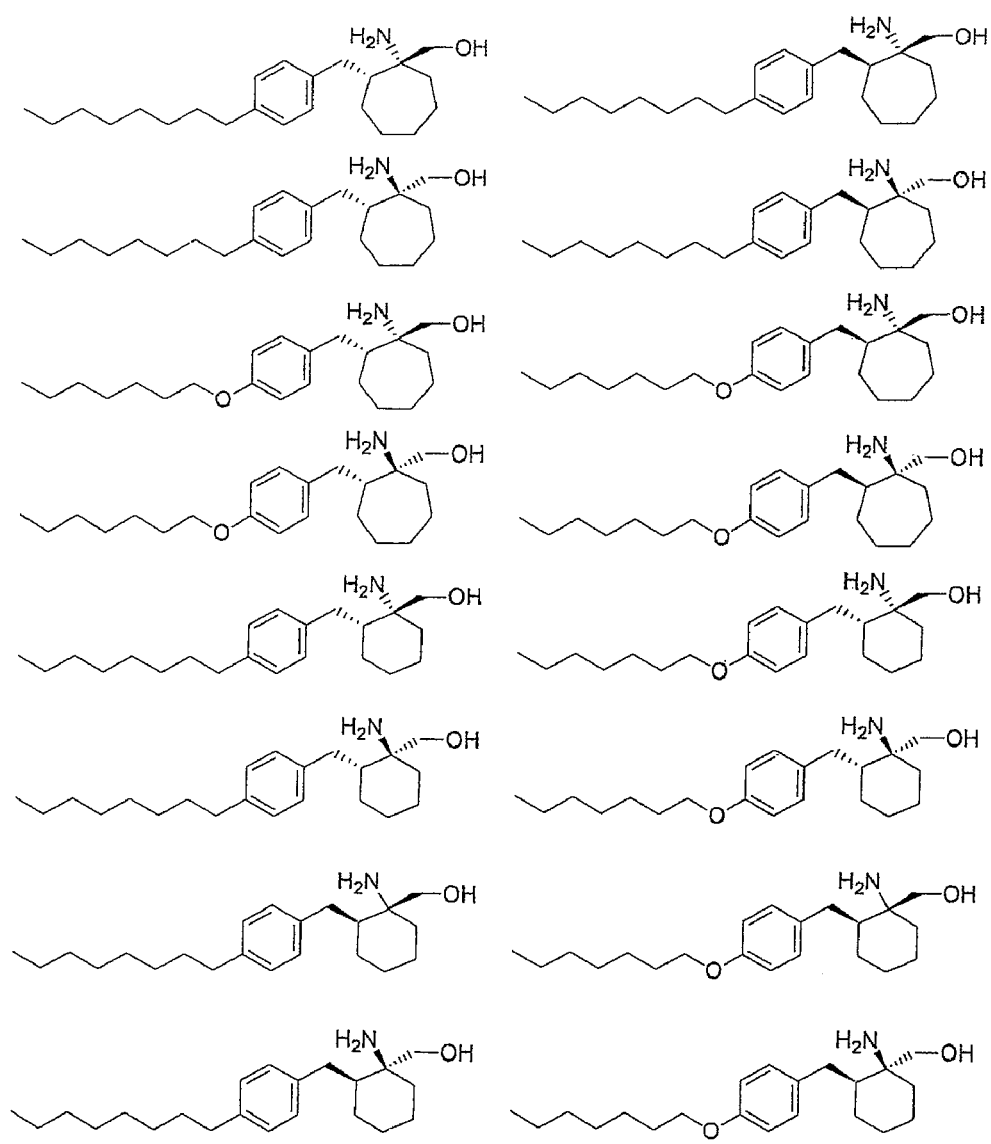
FIG. 6 illustrates additional compounds of Formula II.

Additional exemplary compounds of formula (II) are illustrated in FIG. 6.

Additional exemplary compounds of formula (I) include heteroatoms (e.g., N, S, O) or double bonds in the cycloalkyl ring include the structures below:

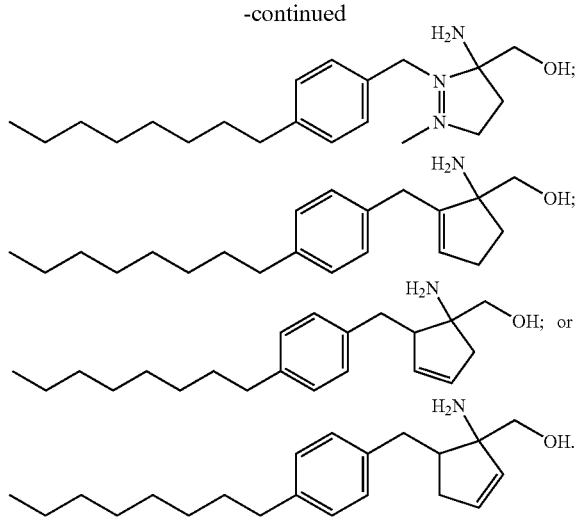

The invention also provides esters of the compounds of formula (I) or formula (II), where the formation of the ester can convert the compounds to pro-drugs to enhance administration, e.g., increase oral availability. In addition, the invention also provides pharmaceutically acceptable salts of the compounds of formula (I) or formula (II). Further, the invention provide all possible isomers of the structures described by formula (I) or formula (II), noting that when n is one (cyclobutane) the compound is symmetric and lacks chiral centers, but cis and trans forms exist.

Pharmaceutical compositions comprising one of more compounds of the invention can be administered to a subject in need thereof by any number of routes and means including, but not limited to, topical, oral, buccal, intravenous, intramuscular, intra arterial, intramedullary, intrathecal, intraventricular, transdermal, subcutaneous, intraperitoneal, intranasal, enteral, topical, sublingual, vaginal, ophthalmic, pulmonary, or rectal means. The oral route is typically employed for most conditions requiring the compounds of the invention. Preference is given to intravenous injection or infusion for the acute treatments. For maintenance regimens, the oral or parenteral, e.g. intramuscular or subcutaneous, route is preferred.

In accordance with one embodiment, a composition is provided that comprises a compounds of formula (I), formula (II), pharmaceutically acceptable salts, esters, analogs, derivatives, modifications or combinations thereof, and albumin. More particularly, the composition comprises compounds of formula (I), formula (II), pharmaceutically acceptable salts, esters, analogs, derivatives, modifications or combinations thereof, a pharmaceutically acceptable carrier and 0.1-1.0% albumin. Albumin functions as a buffer and improves the solubility of the compounds. In one aspect, albumin is not added.

In one embodiment, the pharmaceutical compositions useful for practicing the invention may be administered to deliver a dose of between 1 ng/kg/day and 100 mg/kg/day. In another embodiment, the pharmaceutical compositions useful for practicing the invention may be administered to deliver a dose of between 1 ng/kg/day and 100 g/kg/day.

Pharmaceutically acceptable carriers which are useful include, but are not limited to, glycerol, water, saline, ethanol, and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non toxic parenterally acceptable diluent or solvent, such as water or 1,3 butane diol, for example. Other acceptable diluents and solvents include, but are not limited to, Ringer's solution, isotonic sodium chloride solution, and fixed oils such as synthetic mono- or di-glycerides.

Compounds which are identified using any of the methods described herein may be formulated and administered to a subject for treatment of any of the diseases and disorders described herein. However, the use of compounds of the invention should not be construed to include only the diseases and disorder described herein. Preferably, the subject is a human.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions for administration to humans, it will be understood by the skilled artisan that such compositions are suitable for administration to animals of all sorts. Modification of pharmaceutical compositions for administration to humans in order to render the compositions for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, and mammals, including commercially relevant mammals such as cattle, pigs, horses, sheep, cats, and dogs.

A pharmaceutical composition of the invention may be prepared, packaged, or sold in bulk, as a single unit dose, or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers.

Controlled- or sustained-release formulations of a pharmaceutical composition of the invention may be made using conventional technology.

In some cases, the dosage forms to be used can be provided as slow or controlled-release of one or more active ingredients therein using, for example, hydroxypropylmethyl cellulose, other polymer matrices, gels, permeable membranes, osmotic systems, multilayer coatings, microparticles, liposomes, or microspheres or a combination thereof to provide the desired release profile in varying proportions. Exemplary controlled-release formulations known to those of ordinary skill in the art, including those described herein, can be readily selected for use with the pharmaceutical compositions of the invention. Thus, single unit dosage forms for oral administration, such as tablets, capsules, gelcaps, and caplets that are adapted for controlled-release are encompassed.

Controlled-release formulations can be designed to initially release an amount of drug that promptly produces the desired therapeutic effect, and gradually and continually release of other amounts of drug to maintain this level of therapeutic effect over an extended period of time. In order to maintain this constant level of drug in the body, the drug must be released from the dosage form at a rate that will replace the amount of drug being metabolized and excreted from the body. Controlled-release of an active ingredient can be stimulated by various inducers, for example pH, temperature, enzymes, water, or other physiological conditions or compounds.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

An "oily" liquid is one which comprises a carbon-containing liquid molecule and which exhibits a less polar character than water.

A formulation of a pharmaceutical composition of the invention for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations for oral administration include, but are not limited to, a powdered or granular formulation, an aqueous or oily suspension, an aqueous or oily solution, a paste, a gel, a toothpaste, a mouthwash, a coating, an oral rinse, or an emulsion. The terms oral rinse and mouthwash are used interchangeably herein.

A tablet comprising the active ingredient may, for example, be made by compressing or molding the active ingredient, optionally with one or more additional ingredients. Compressed tablets may be prepared by compressing, in a suitable device, the active ingredient in a free flowing form such as a powder or granular preparation, optionally mixed with one or more of a binder, a lubricant, an excipient, a surface-active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface-active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide for pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of the disclosed pharmaceutical composition for oral administration may be prepared, packaged, and sold either in liquid form or in the form of a dry product intended for reconstitution with water or another suitable vehicle prior to use.

Injectable formulations may be prepared, packaged, or sold in unit dosage form, such as in ampules or in multi dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (e.g., powder or granular) form for reconstitution with a suitable vehicle (e.g., sterile pyrogen free water) prior to parenteral administration of the reconstituted composition.

A pharmaceutical composition of the invention may be prepared, packaged, or sold in a formulation for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

"Additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. See Genaro, ed., 1985, *Remington's Pharmaceutical Sciences*, Mack Publishing Co., Easton, Pa., which is incorporated herein by reference.

The compound can be administered to a subject as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type, and age of the subject, etc.

The invention also provides a pharmaceutical pack or kit comprising one or more containers filled with one or more of the ingredients of the pharmaceutical compositions of the invention. In accordance with one embodiment, a kit is provided for treating a subject in need of immuno-modulation. Preferably, the subject is a human. In one embodiment, the kit comprises one or more of the S1P analogs of the present invention and may also include one or more known immunosuppressants. These pharmaceuticals can be packaged in a variety of containers, e.g., vials, tubes, microtiter well plates, bottles, and the like. Other reagents can be included in separate containers and provided with the kit; e.g., positive control samples, negative control samples, buffers, cell culture media, etc. Preferably, the kits will also include instructions for use.

Although any methods and materials similar or equivalent to those described herein can be used in the practice or testing of the present invention, the preferred methods and materials are described herein.

One skilled in the art will readily appreciate that the present invention is well adapted to carry out the objects and obtain the ends and advantages mentioned, as well as those inherent therein. The present invention may be embodied in other specific forms without departing from the spirit or essential attributes thereof.

EXAMPLES

The invention is now described with reference to the following examples. These examples are provided for the purpose of illustration only and the invention should in no way be construed as being limited to these examples, but rather should be construed to encompass any and all variations which become evident as a result of the teachings provided herein.

Example 1

(1-amino-2-(4'-octylbenzyl)cyclopentyl)methanol (9)

A.: 2-(4'-iodobenzyl)cyclopentanone (3). 2-Carboethoxycyclopentanone (1) (1.0 eq, 1.56 g, 10.0 mmole) was dissolved in 100 mL of tetrahydrofuran under nitrogen atmosphere at room temperature. Sodium ethoxide (1.10 eq, 748 mg, 11.0 mmole) was added, then 4'-iodobenzyl chloride (1.25 eq, 3.15 g, 12.5 mmole) was introduced and the reaction warmed to reflux and maintained for 6 hours. The reaction was then cooled and the solvent removed in vacuo providing the crude 2-carboethoxy-2-(4'-iodobenzyl)cyclopentanone (2). The crude product was dissolved in aqueous ethanol (10% water v/v) 100 mL, sulfuric acid (0.1 mL) was added and the reaction was refluxed for 6 hours under nitrogen. The reaction was then cooled, diluted with 100 mL ether and extracted with 5% aqueous bicarbonate solution (2×50 mL), then the organic layer was washed with brine and dried over $MgSO_4$. Removal of the solvent in vacuo gave a yellow oil which was purified by flash column chromatography using ethyl acetate/hexanes as eluent to yield 2-(4'-iodobenzyl)cyclopentanone (3) (2.145 g, 7.20 mmole, 72%). (See: *Organic Syntheses, Coll. Vol.* 5, p. 76 (1973); Vol. 45, p. 7 (1965))

B.: 2-(4'-(oct-1-ynyl)benzyl)cyclopentanone (4). 1.1 g (10 mmol) of 1-Octyne was added to a flame dried 25 mL flask charged with a 10 mL THF solution of 1.49 g (5 mmol) of 2-(4'-iodobenzyl)cyclopentanone (3). After degassing for 30 minutes, 2 mL triethylamine, 5 mg of CuI and 10 mg of $Pd(PPh_3)_4$ were added under $N_2$ protection. The reaction was stirred at room temperature for 6 hrs, then the solvent removed in vacuo and residue chromotographed with chloroform eluent to give 1.25 g (93%) as a yellow oil.

$^{13}C$ NMR ($CDCl_3$) δ 220, 143, 132, 127, 122, 91, 80, 46, 42, 39, 32, 31, 29, 29, 23, 20, 14.

C.: 2-(4'-octylbenzyl)cyclopentanone (5). Several drops of formic acid and catalytic amount 5% Pd/C was added to a 25 mL flask charged with 10 mL methanol and 1.25 g (4.75 mmol) of 2-(4'-(oct-1-ynyl)benzyl)cyclopentanone (4). The reaction vessel was flushed with $H_2$, three times, and then mounted with a $H_2$ balloon. After two days under the hydrogen atmosphere, the reaction mixture was exposed to nitrogen, and then filtered through a pad of silica gel. The silica gel plug was washed with ethyl ether (2×25 mL) and the combined organic layers were concentrated to a crude product providing a light yellow oil (1.24 g, 98%).

$^{13}C$ NMR ($CDCl_3$) δ 220, 142, 140, 129, 127, 46, 42, 39, 36, 32, 32, 32, 30, 30, 29, 23, 14.

D.: 1-amino-2-(4'-octylbenzyl)cyclopentanecarbonitrile (6). 2-(4-Octylbenzyl)cyclopentanone (5) 3.20 g (11.8 mmol), sodium cyanide 1.15 g (23.5 mmol) and ammonium chloride 1.25 g (23.5 mmol) were added to 20 mL of ammonium hydroxide. The mixture was stirred vigorously for 12 hours at room temperature, then poured into a separating funnel and extracted twice with 10 mL of methylene chloride. The organic layers were combined, dried and then concentrated to give a crude yellow oil (3.30 g, ~100%). The crude product is used for next step without further purification. (See: *J. Med. Chem.*, 1986, 29, 1988-1995).

E.: 1-amino-2-(4'-octylbenzyl)cyclopentanecarboxylic acid (7). 1-Amino-2-(4'-octylbenzyl)cyclopentanecarbonitrile (6) (3.3 g, 11.2 mmol) and 50 mL concentrated hydrochloric acid was heated to 70° C. and stirred overnight. The resulting clear aqueous solution was evaporated to dryness. 10 mL water was added and dried again. This process was repeated several times. The crude product was washed with water and acetone to give a white fine powder which was used in the next step without further purification. The crude yield was 1.71 g (45%).

$^{13}C$ NMR ($d^6$-DMSO) δ 175, 141, 140, 64, 51, 46, 45, 44, 36, 35, 35, 34, 32, 32, 29, 29, 23, 15.

F.: (1-amino-2-(4'-octylphenyl)cyclopentyl)methanol (8). 1-Amino-2-(4'-octylbenzyl)cyclopentanecarboxylic acid (7)

(63.4 mg, 0.2 mmol) and 27 mg (0.6 mmol) sodium borohydride were dissolved in 3 mL of THF. After the solution was cooled to 0° C., 51 mg (0.2 mmol) $I_2$ was dissolved in 1 mL THF and added dropwise. Then the vessel was fitted with a condenser and the reaction mixture was refluxed under $N_2$ for 5 hours. Excess $NaBH_4$ was then quenched with methanol and the solvent was removed under vacuum. Water (2 mL) and methylene chloride (5 mL) was added was added to the residue and the mixture was stirred for about 1 hr until the organic layer became clear. The organic phase was collected and aqueous phase was further extracted twice with methylene chloride (5 mL fractions). The combined organic extraction was dried and concentrated to give 43 mg (71%) of crude product. Further purification on TLC with methanol/chloroform (5:95) gave 13 mg clear oil. *J. Org. Chem.*, 1993, 58, 3568-3571.

$^{13}$C NMR ($CD_3COCD_3$) δ 141, 128, 127, 96, 45, 44, 43, 35, 35, 33, 33, 32, 32, 29, 29, 29, 23, 13.

Example 2

(1-amino-3-(4-octylphenyl)cyclopentyl)methyl dihydrogen phosphate (9)

(1-amino-3-(4-octylphenyl)cyclopentyl)methyl dihydrogen phosphate (9). 1 mL 85% $H_3PO_4$ was added dropwise into 0.5 g of $P_2O_5$, the acid-anhydride mixture was then heated at 100° C. for 1 hour under nitrogen protection. Another 0.5 g of $P_2O_5$ and 30 mg of (1-amino-2-(4'-octylphenyl)cyclopentyl)methanol (8) were added to the polyphosphoric acid solution and heated for 5 hours at 100° C. After cooling down to room temperature, 10 mL of ice cold water was added to reaction mixture. The crude product precipitated as white solid which was filtered and washed with cold water. A light green colored product (31 mg, 82%) was collected after vacuum drying. The mass spectrum gave only two peaks: M+1=398.4 (indicative of the desired phosphorylated material 9 and 318.4 (characteristic of the dephosphorylated or starting material 8).

Example 3

Sphingosine Kinase Assay

The activity of the disclosed compounds was evaluated using recombinant human and mouse sphingosine kinase isoforms in an in vitro assay comparing sphingosine, and FTY720, with test compounds VPC122093, VPC122096, and VPC122097. Recombinant sphingosine kinase type 1 or 2 (SPHK1, SPHK2) is prepared by forcing the expression of the mouse or human recombinant enzyme by transfecting the relevant plasmid DNA into HEK293T cells. After about 60 hours the cells are harvested, broken and the non-microsomal (e.g., soluble) fraction is retained.

Figure 2:
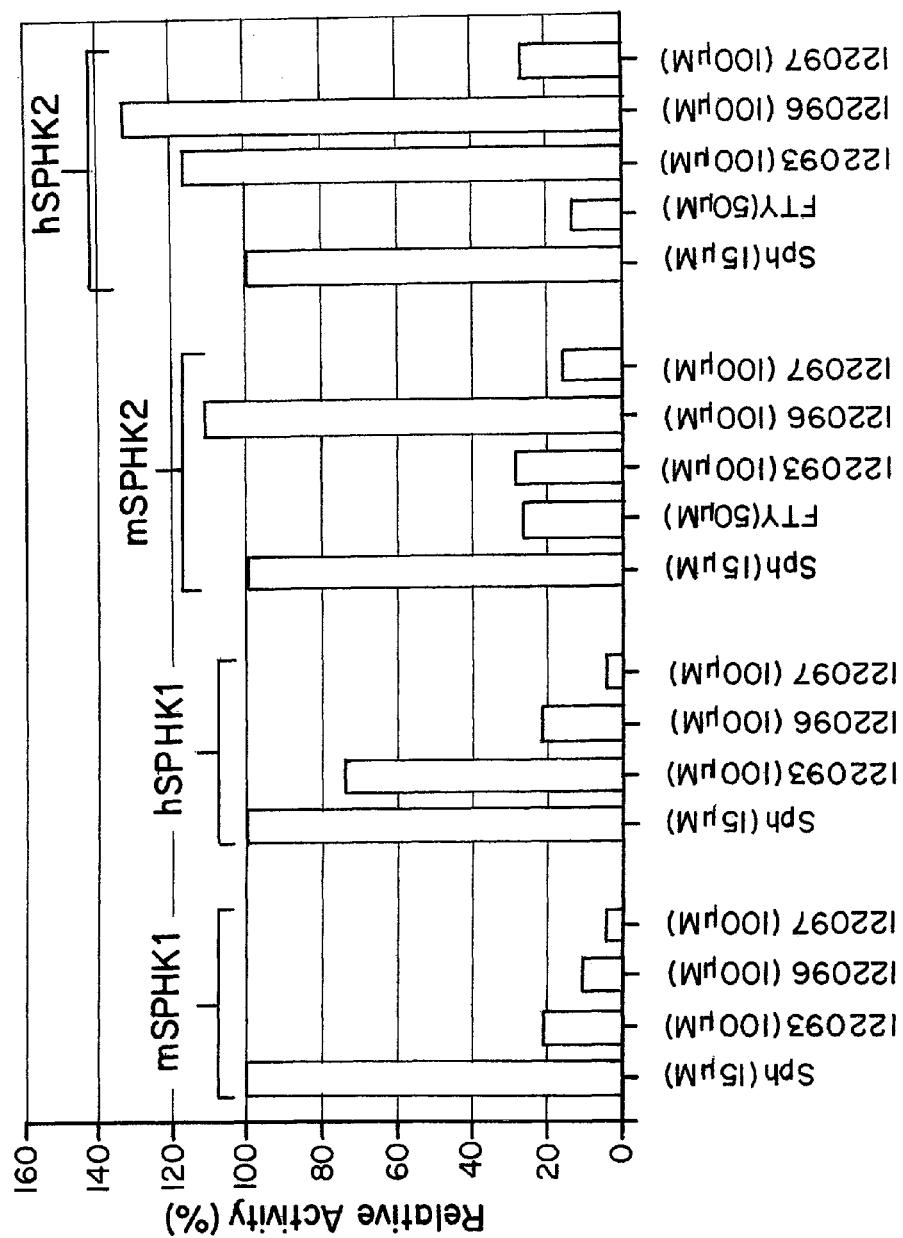
FIG. 2 is a graphic illustration of the in vitro assay comparing sphingosine, and FTY720, with test compounds VPC122093, VPC122096 and VPC122097 as substrates for human and mouse sphingosine kinase types 1 and 2 (SPHK1 and SPHK2).

The broken cell supernatant fluid containing the recombinant enzyme is mixed with substrates, sphingosine, FTY720, or the test compounds (VPC122096, VPC122097, or VPC122093) and gamma-32P-ATP. The concentration of substrates was: sphingosine, 15 micromolar; FTY720, 50 micromolar; VPC compounds, 100 micromolar. The supernatant homogenates from HEK293T cells expressing indicated SPHK isoform with 32P-ATP and the substrates were incubated for 1 hour at 37° C. After the reaction, the lipids were extracted with acidified chloroform/methanol, separated by thin layer chromatography, bands containing S1P visualized by autoradiography, isolated and quantified by scintillation counting. The results are illustrated in FIG. 2.

Example 4

Lymphopenia Assays

The test compounds VPC122096 (benzylcyclopentyl), VPC122093 (benzylcyclohexyl) or VPC122097 (benzylcycloheptyl) compounds are dissolved in 2% hydroxypropyl beta-cyclodextrin and administered to mice by oral gavage at doses from 0.01 to 10 mg/kg body weight. After 24 hours (or other specified times), the mice are lightly anesthetized and ca. 0.1 ml of blood is drawn from the orbital sinus. The number of lymphocytes (in thousands per microliter of blood; normal is 4-11) is determined using a Hemavet blood analyzer. There were three mice per group, male, 10-11 weeks old, and the strain was mixed sv129×C57BL/6.

Example 4A

Figure 3:
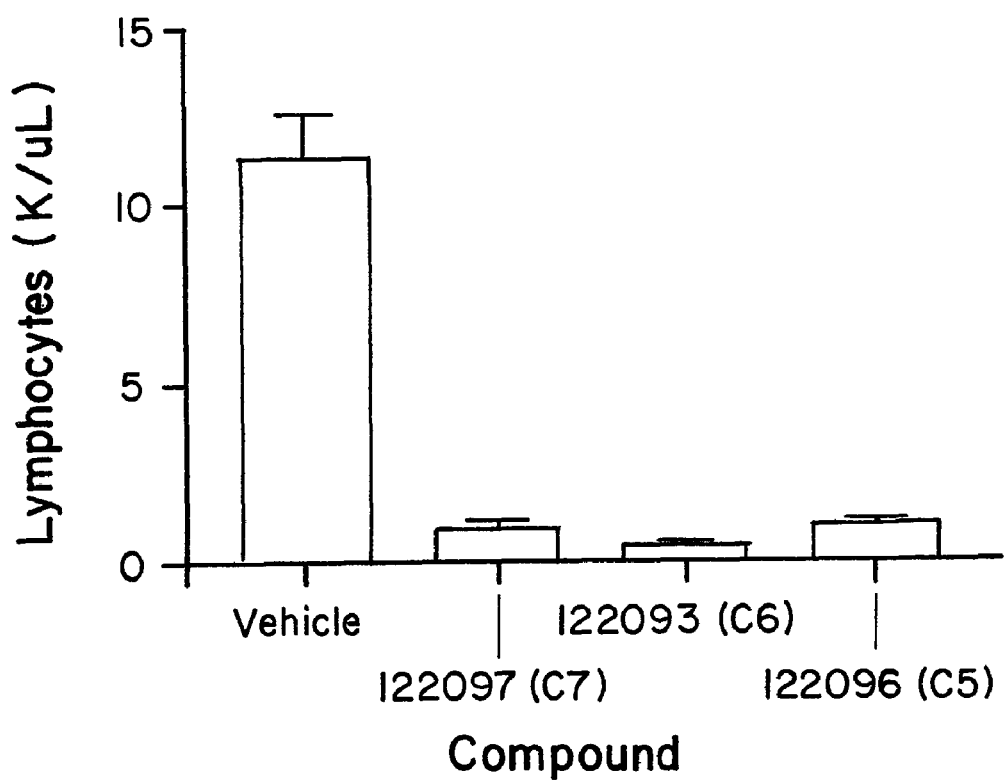
FIG. 3 is a graphic illustration of circulating lymphocyte counts in mice after oral administration (gavage) of a single dose (10 mg/kg) of VPC122096 (cyclopentyl), VPC122093 (cyclohexyl) or VPC122097 (cycloheptyl).

The test compounds VPC122096, VPC122097, or VPC122093 were dissolved in 2% aqueous hydroxypropyl beta-cyclodextrin and introduced into mice by oral gavage at 10 mg/kg (Three mice per group). Blood was drawn after 18 hours and examined. The test compounds evoked lymphopenia. The results are illustrated in FIG. 3.

Example 4B

Figure 4:
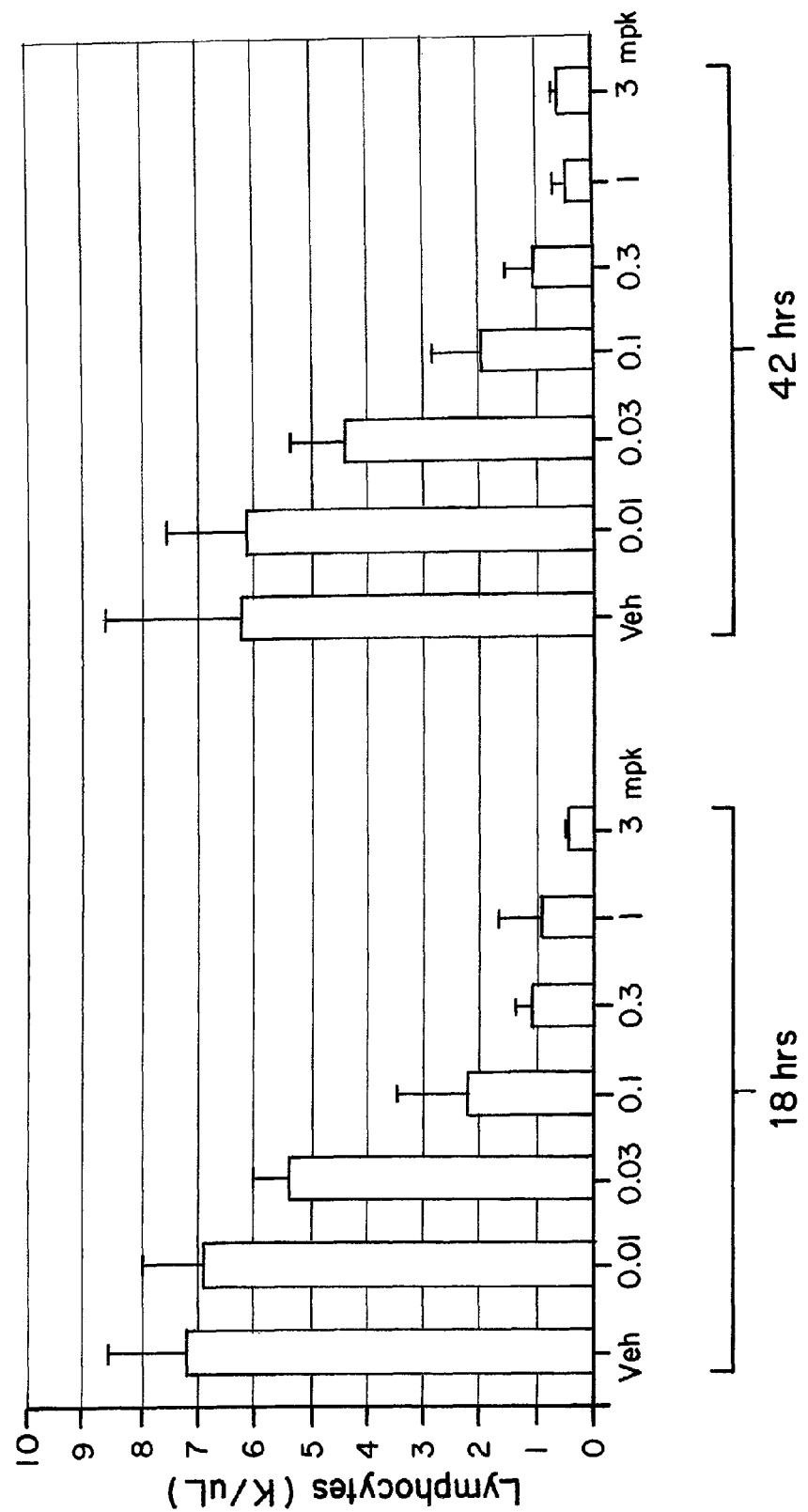
FIG. 4 is a graphic illustration of total blood lymphocyte counts following administration of various doses of VPC122096 or vehicle to mice.

The test compound VPC122096, was dissolved in 2% aqueous hydroxypropyl beta-cyclodextrin (vehicle) and administered to mice orally (gavage) at doses of 0.01 mg/kg, 0.03 mg/kg, 0.1 mg/kg, 0.3 mg/kg, 1 mg/kg, and 3 mg/kg to provide a dose response curve (three-four mice per group, adult, C57Bl/6 strain). The blood samples were taken at 18 hours and 42 hours. Three mice per group, male, 10-11 week old sv129/C57Bl6 strain. The results are illustrated in FIG. 4. The ordinate represents lymphocytes in K/μl. The abscissa represents time in days after administration of a single dose. The ordinate represents lymphocytes in K/μl. The abscissa represents dose in milligram compound per kilogram body weight (mpk).

Example 4C

Figure 5:
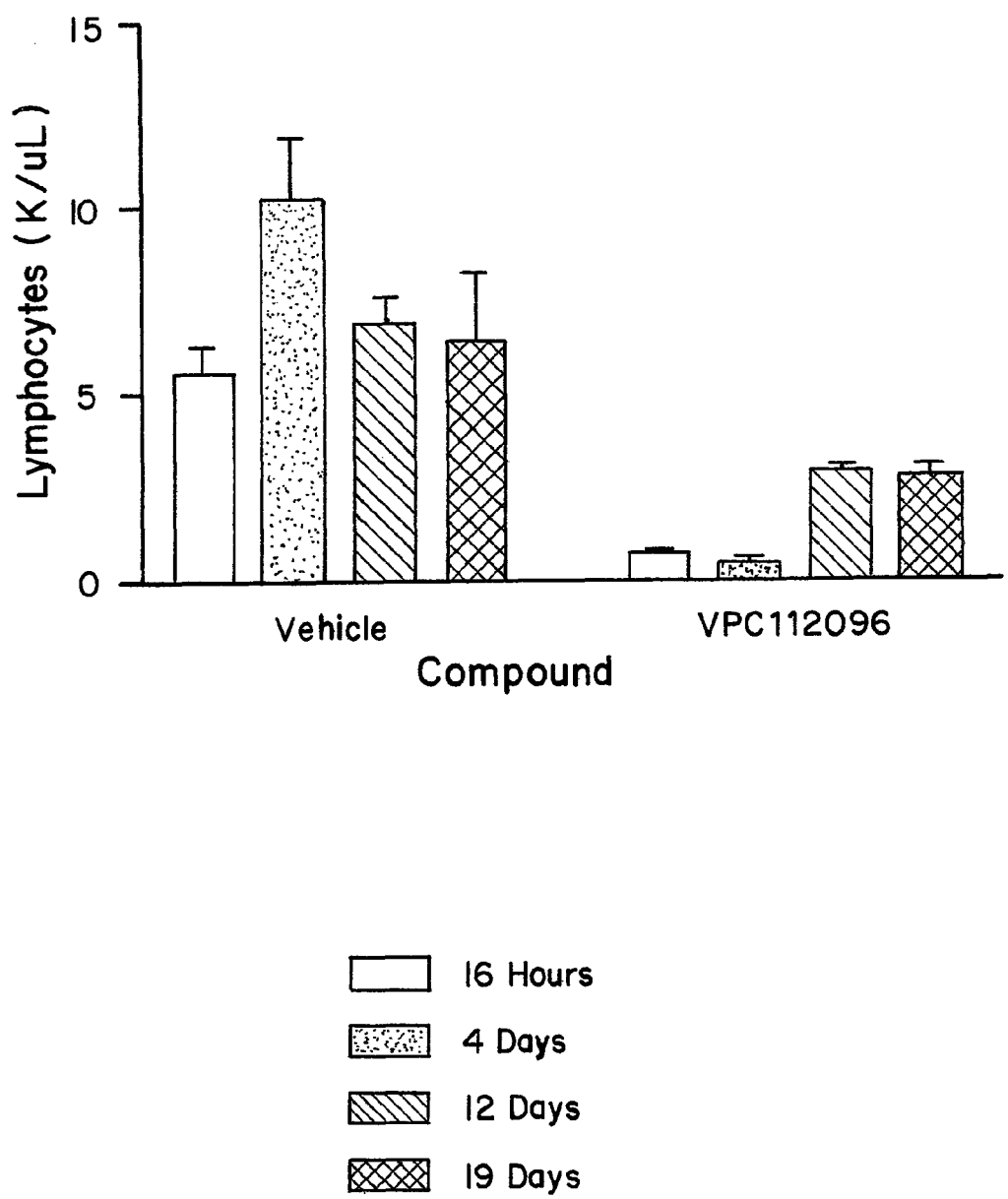
FIG. 5 is a graphic illustration of the results of circulating lymphocyte counts assay at various times following oral administration (gavage) of a single concentration of VPC122096 (1.0 mg/kg) in 2% hydroxypropyl β-cyclodextrin (vehicle control), 3 mice per group.

The duration of the effect of the test compounds was evaluated after administration of test compound VPC122096, dissolved in 2% aqueous hydroxypropyl beta-cyclodextrin (vehicle) and administered to mice orally (gavage). The test compound evoked a long lasting lymphopenia. The blood samples were taken at 16 hours, 4 days, 12 days, and 19 days. FIG. 5 illustrates total blood lymphocyte count following the single dose of VPC122096 or vehicle. A single $ED_{95}$ dose of VPC122096 can cause lymphopenia in mice for a week or more.

The abbreviations used herein have their conventional meaning within the clinical, chemical, and biological arts. In the case of any inconsistencies, the present disclosure, including any definitions therein will prevail.

The invention should not be construed to be limited solely to the assays and methods described herein, but should be construed to include other methods and assays as well. Other methods which were used but not described herein are well known and within the competence of one of ordinary skill in the art of chemistry, biochemistry, molecular biology, and clinical medicine. One of ordinary skill in the art will know that other assays and methods are available to perform the procedures described herein.

The disclosures of each and every patent, patent application, and publication cited herein are expressly incorporated herein by reference in their entirety into this disclosure. Illustrative embodiments of this disclosure are discussed and reference has been made to possible variations within the scope of this disclosure. These and other variations and modifications in the disclosure will be apparent to those skilled in the art without departing from the scope of the disclosure, and it should be understood that this disclosure and the claims shown below are not limited to the illustrative embodiments set forth herein.

The invention claimed is:

1. A compound of the formula:

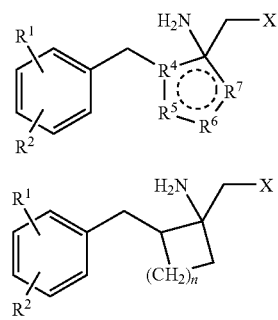

wherein $R^4$ is C, CH, or N; $R^5$, $R^6$ and $R^7$ are independently CH, $CH_2$, O, S, N, or $NR^a$;

X is hydroxyl, carboxylic acid, methylene carboxylic acid, alpha-substituted carboxylic acid, phosphate, phosphonate, or alpha-substituted phosphonate;

$R^1$ is hydrogen, halo, tri-fluoromethyl, $(C_1-C_{10})$alkyl, halo $(C_1-C_{10})$alkyl, hydroxy-$(C_1-C_{10})$alkyl, $(C_1-C_{10})$ alkoxy $(C_1-C_{10})$alkyl, or cyano$(C_1-C_{10})$alkyl; and $R^2$ is hydrogen, halo, $(C_1-C_{20})$alkyl, $(C_1-C_{20})$alkoxy; $(C_2-C_{26})$ alkoxyalkyl; $(C_2-C_{20})$alkenyl, $(C_2-C_{20})$alkynyl, $(C_3-C_{12})$cycloalkyl, $(C_1-C_{20})$alkyl-$(C_3-C_{12})$cycloalkyl, $(C_6-C_{10})$ aryl, $(C_1-C_{20})$alkyl$(C_6-C_{10})$aryl, $(C_6-C_{10})$aryl$(C_1-C_{20})$ alkyl, and aryl substituted arylalkyl; wherein one or more of the carbon atoms in the $R^2$ groups can be independently replaced with non-peroxide oxygen, sulfur or $NR^a$;

the alkenyl, alkynyl, cycloalkyl, aryl, heterocyclic, or heteroaryl groups of $R^1$, $R^2$, or X are optionally substituted with 1, 2, 3, or 4 groups where the substituent groups are independently hydroxy, halo, cyano, $(C_1-C_{10})$alkyl, $(C_1-C_{10})$alkoxy, $C_6$-aryl, $(C_7-C_{24})$arylalkyl, oxo (=O), or imino (=$NR^a$); $R^a$ is hydrogen, or $(C_1-C_{10})$alkyl; and n is 0, 1, 2, 3, or 4;

⌒  
(   )  
 ⌣ indicates one or more optional double bonds, and the alkyl groups of $R^a$ are optionally substituted with 1, or 2 hydroxy groups; or a pharmaceutically acceptable salt or ester thereof.

2. The compound of claim 1, of Formula (II):

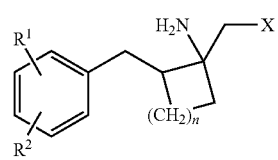

wherein X is hydroxyl, phosphate, phosphonate, or alpha-substituted phosphonate;

wherein $R^1$ is hydrogen, halogens, $(C_1-C_6)$ alkyl, halo$(C_1-C_6)$ alkyl, hydroxy$(C_1-C_6)$ alkyl, alkoxy$(C_1-C_6)$ alkyl, or cyano$(C_1-C_{-6})$ alkyl;

$R^2$ is alkyl, alkenyl, alkynyl, alkyl substituted aryl, alkyl substituted cycloalkyl, arylalkyl or arylalkyl substituted aryl; and n is 0, 1, 2 or 3; or a pharmaceutically acceptable salt thereof.

3. The compound of claim 1, wherein $R^1$ is fluorine or chlorine.

4. The compound of claim 1, wherein X is hydroxy or $OPO_3H_2$.

5. The compound of claim 4, wherein X is $OPO_3H_2$.

6. The compound of claim 4, wherein X is hydroxy.

7. The compound of claim 1, wherein alpha-substituted phosphonate is —$CHFPO_3H_2$, —$CF_2PO_3H_2$, —$CHOHPO_3H_2$, —$C(=O)PO_3H_2$ or —$OPO_2SH_2$.

8. The compound of claim 7, wherein alpha-substituted phosphonate is —$CHFPO_3H_2$, —$CF_2PO_3H_2$, —$CHOHPO_3H_2$, or —$C(=O)PO_3H_2$.

9. The compound of claim 1, wherein $R^1$ is hydrogen.

10. The compound of claim 1, wherein $R^2$ is alkyl having 5, 6, 7, or 8 carbon atoms.

11. The compound of claim 10, wherein $R^2$ is heptyl, octyl, nonyl, —O—heptyl, or $CH_3$—O—$CH_2$—$CH_2$—$CH_2$—$CH_2$—$CH_2$—$CH_2$—.

12. The compound of claim 11, wherein $R^2$ is octyl.

13. The compound of claim 1, wherein n is 1 or 2.

14. The compound of claim 1, wherein the $R^2$ group is placed para to the cycloalkyl ring.

15. The compound of claim 1, wherein the cycloalkyl group has the formula:

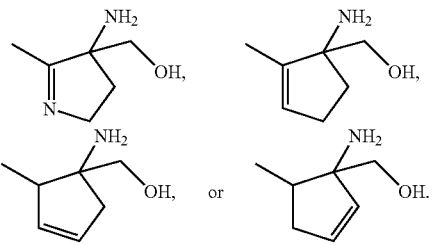

16. The compound of claim 1, wherein the $R^1$ group is ortho or meta to $R^2$.

17. The compound of claim 1, wherein the $R^2$ group is para to the benzylic cycloalkyl group.

18. The compound of claim 2, having the formula:

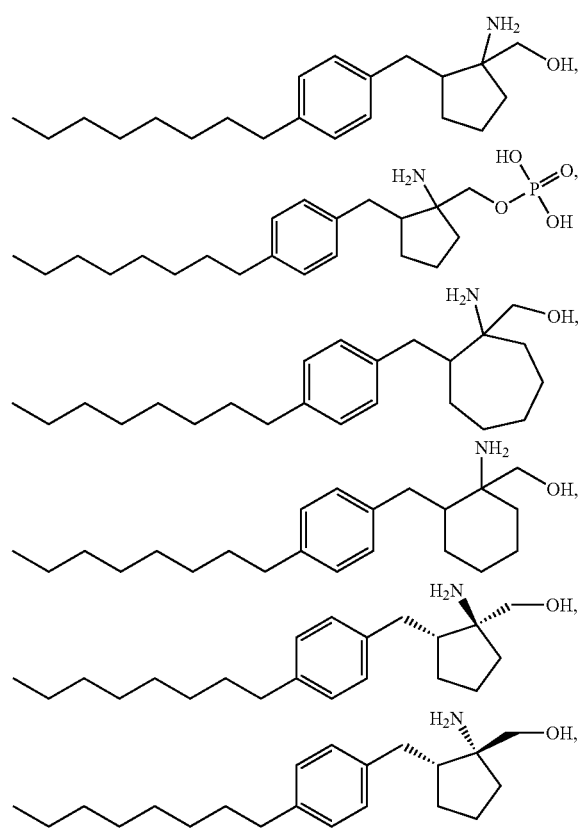

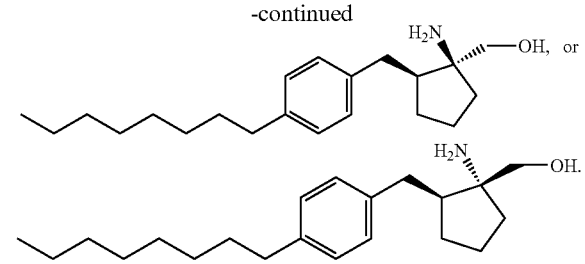

19. A pharmaceutical composition comprising a compound of claim 1 and a pharmaceutically acceptable carrier.

20. A method for treatment of a pathological condition or symptom in a mammal, wherein the activity of sphingosine 1-phosphate receptors is implicated and agonism of such activity is desired, comprising administering to said mammal an effective amount of a compound of claim 1.

21. The method of claim 20, wherein the pathological condition is an autoimmune disease.

22. The method of claim 21, wherein the autoimmune disease is uveitis, type I diabetes, rheumatoid arthritis, inflammatory bowel diseases, or multiple sclerosis.

23. The method of claim 22, wherein the autoimmune disease is multiple sclerosis.

24. A method for treatment of a pathological condition or symptom in a mammal, wherein the activity of S1P lyase is implicated and inhibition of the S1P lyase is desired, comprising administering to said mammal an effective amount of a compound of claim 1.

25. A kit for administering at least one compound of claim 1 to a patient in need thereof, said kit comprising a pharmaceutical composition comprising at least one compound, an applicator, and instructional material for the use thereof.

* * * * *